United States Patent [19]

Vass et al.

[11] 3,966,554

[45] June 29, 1976

[54] PROCESS FOR THE PRODUCTION OF A PROTEIN-VITAMIN CONCENTRATE BY USING YEASTS FROM ANIMAL OR VEGETABLE FATS AND FOR ITS TRANSFORMATION INTO A PRODUCT

[75] Inventors: Károly Vass; György Kárpáti; Éva Széchenyi-Márton; Ferenc Simek, all of Budapest, Hungary

[73] Assignee: Novex RT, Hungary

[22] Filed: June 20, 1973

[21] Appl. No.: 371,706

[30] Foreign Application Priority Data

June 20, 1972 Hungary............................ KO-2520

[52] U.S. Cl................................. 195/30; 195/82; 426/56; 426/60
[51] Int. Cl.².......................................... A23J 1/18
[58] Field of Search................ 195/30, 82, 28 R, 83; 426/33, 62, 204, 24, 42, 52, 53, 56, 60

[56] References Cited
UNITED STATES PATENTS

| | | | |
|---|---|---|---|
| 3,095,357 | 6/1963 | Fulde............................... | 195/28 R |
| 3,475,274 | 10/1969 | Harned............................. | 195/28 R |
| 3,619,368 | 11/1971 | Woldendorp....................... | 195/30 |
| 3,782,967 | 1/1974 | Eriksen et al...................... | 426/62 |

*Primary Examiner*—Lionel M. Shapiro
*Attorney, Agent, or Firm*—Young & Thompson

[57] ABSTRACT

A protein-vitamin concentrate having a high proportion of dry yeast and a protein content of at least 50% and particularly rich in B-vitamins, is produced by cultivating yeast in a culture medium containing animal or vegetable fat as a source of carbon, at a pH of 4 to 6 and a temperature of 30° to 40°C. and an aeration intensity of 150 to 300 cubic meters of air per square meter of fermenter base area per hour, the culture containing also an ammonium salt or carbamide as a source of nitrogen, the nitrogen content of the culture medium being 0.1–0.2%, the N:P ratio being 4:1, potassium and chloride ions being present in the form of 0.1–0.2% KCl, and Mg and $SO_4$ ions being present as 0.080–0.1% $MgSO_4$.

4 Claims, No Drawings

PROCESS FOR THE PRODUCTION OF A PROTEIN-VITAMIN CONCENTRATE BY USING YEASTS FROM ANIMAL OR VEGETABLE FATS AND FOR ITS TRANSFORMATION INTO A PRODUCT

It is known that in nearly all the countries of the world there is an ever increasing demand for full value, economically producible and relatively inexpensive protein sources which are suitable for the partial complementing of animal proteins or for completing the nutrients (cereals, greens) which do not contain full value proteins. For this purpose micro-organisms, especially the yeasts, are very suitable because they may be produced industrially, their growth rate in contrast to that of animals or cultivated plants is very great, approximately half of the dry material of the cell is protein, the amino acid composition of which approaches the reference protein composition established by the FAO. For information we set out the essential amino acid composition of the FAO reference, of a whole egg, and of yeast.

| Amino acid (g N/16 g protein nitrogen) | FAO ref.[x] | Whole egg[+] | Yeast[o] |
|---|---|---|---|
| Leucine | 4.8 | 8.8 | 6 – 8 |
| Iso-leucine | 4.2 | 4.2 | 4 – 6 |
| Lysine | 4.2 | 7.2 | 4 – 8 |
| Methionine | 2.2 | 3.85 | 1.5 – 2 |
| Cistine | 2.0 | | 0.8 – 1 |
| Phenylalanine | 2.8 | 5.7 | 3 – 5 |
| Tryptophan | 1.4 | 1.3 | 1 – 1.5 |
| Valine | 4.2 | 8.8 | 4 – 6 |
| Tyrosine | 2.8 | 3.6 | 2.5 – 4 |
| Threonine | 2.8 | 5.3 | 2 – 6 |

[x]FAO Nutritional Studies N°16, Rome, 1957
[+]World Protein Resources Amcr. Chem. Soc. 1966, 2nd Chapter
[o]Literature data and our own measurements It is known from practice and from the technical literature that certain micro-organisms or their special strains are suitable for proliferating in suitable conditions in a culture medium containing various sugars (hexoses, pentoses), alcohols (methanol, ethanol, glycerol), straight chain hydrocarbon acids (fatty acids) and alkanes, and for producing cell material of high protein and vitamin content.

In practice the hitherto known processes refer to the production of such yeast strains which are employed as fermentation cultures (baking yeast, wine yeast) or as cell material serving as animal fodder and containing protein and having non-fermenting properties (fodder yeast). In some countries initial steps have been taken to use the fermenting type yeast strains for feeding purposes (as additives or as nutritive food components) by inactivation and drying.

The yeast strains and the culture media serving as energy source (carbon source) used for this purpose in industrial practice are as follows:

| Yeast strains: | Substrates: |
|---|---|
| Saccharomyces cerevisiae | molasses |
| Saccharomyces fragilis | whey of milk |
| Torulopsis utilis | molasses swillings |
| candida guilliermondii | sulphite slops |
| Candida lipolytica | cellulose and starch hydrolisates alkanes |

The basic principles of known processes are described in textbooks, such as

Telegdy Kováts-Holló: Élelmezési iparok (Food industries) II. Budapest 1962;
Mateles, R. I., Tannenbaum, S. R.: Single-Cell Protein, M.I.T. Press, Cambridge-London, 1968;
Simon, P., Meunier, R.; Microbiologie Industrielle et Genie Biochimique, Masson et Cie., Paris, 1970;
Cook, A. H.: Chemistry and Biology of yeasts, Academic Press Inc., New York, 1958.

In addition, without attempting a complete survey, we mention below a few more recent patents in this field for demonstrating the latest developments:

Tettex, A.G., Zurich: Swiss patent application No. 15621/65; Kontinuierliches Verfahren zur Herstellung von Hefe insbesondere Backhefe;
Esso Research and Engineering Company, New Jersey: Dutch Pat. No. 6405870/1965: Wekwijze voor het bereiden van een eiwitrijk voedsel;
Vyurst, L. S. V.: Soviet Pat. No. 214473/1968: Sposob vyrashchivaniya kormovykh drozhei;
Deutsche Akademie der Wissenschaften, Berlin (G.D.R.): G.D R. Pat. No. 13645/67; Process for synthesising microbiological cell material in mineral culture medium;
V. V. Challik, Martinson L. V.: Soviet Pat. No. 217330/1968: Sposob proizdvostva kormovykh drozhei;
British Petroleum Co.: French Pat. No. 1,505,489 (1966): Perfectionnements a la production de microorganismes a parti d'hydrocarbures;
British Petroleoum Co.: French Pat. No. 1,553,602 (1968): Procédé de culture de microorganismes et produits obtenus.

In addition to these, descriptions of methods of growing microorganisms and recovering the products may be found in British Pat. Nos. 914,567, 915,568, 1,017,584, 1,021,697, 1,021,698, 1,049,066, 1,049,067, 1,059,881, 1,059,882, 1,059,887, 1,059,889, 1,059,890; French Pat. No.: 1,334,466 and Hungarian Pat. Nos. 152,495, 152,628, 152,817, 152,818, 152,819, 153,696, 152,949, 152,950 and 152,951.

It is a disadvantage of all the energy sources used, that either they are not available in sufficient quantity (molasses, whey of milk) or they require more or less complicated preparation (sulphite waste liquor, cellulose) or primarily health problems prevent their use (alkanes) and/or they can be regarded as economic only under certain circumstances.

Almost simultaneously with the shift of nutrition demands towards proteins in many countries of the world, there is an ever greater surplus in fats, primarily animal fats. Hitherto these fats have not been used or could not be used for nutritive purposes and have been used as washing means (soaps) or it has been attempted to utilize them as an additive to mixed fodder. However, their use is more and more restricted by the manufacture of synthetic detergent and their direct use as fodder is not economical.

We have found that the fats regarded as surplus from the point of view of feeding may be rendered useful by micro-biologically transforming approximately one half of the fats into biologically valuable protein and we obtain a product through the simultaneously formed valuable vitamins and other biologically useful cell materials which produce is a protein-vitamin concentrate directly suitable for human and animal consumption.

Thus our invention concerns the micro-biological production of a protein-vitamin concentrate directly usable as human food or animal fodder characterized in that the previously adapted micro-organisms are grown or proliferated on animal or vegetable fat serving as a source of carbon and energy in a fermenter and in a culture medium containing minerals and at appropriate pH and temperature under intensive ventilation, then the resulting bio-mass is separated from the liquor in a separator and is used in a pressed or dried form.

If desired the product is formed into a preparation directly usable for human consumption or animal fodder, in given cases it may be mixed with other fodder stuffs and thus food or fodder of increased nutritive value may be produced.

The product made according to the invention may be used for:

a. producing nutritive foods,
b. enriching low-protein food preparations,
c. completing foods and products of an unsuitable amino acid composition,
d. producing preparations (sauces, powders etc) for complementing food,
e. manufacturing dietetic foods and products rich in B-vitamin and protein,
f. manufacturing products enriched in protein for cases of special demand (sportsmen, heavy physical workers),
g. complementing animal fodder concentrates.

The process differs from current practice or from processes known in the technical literature for proliferating micro-organisms in that 1. animal or vegetable fat is used as energy source (carbon source),
2. the fats used are employed without any preparation (hydrolysis),
3. for this purpose micro-organisms are employed which are capable, after adaptation, of producing cell material, usable for direct human consumption.

In addition to the advantage of using a carbon source (animal or vegetable fat) not requiring preparation, it is an advantage of the process that it does not require special apparatus or a partial process and the cultivation of the micro-organisms takes place in the conventional manner and in conventional apparatus, and that the cell mass recovered as the product does not require special cleaning since the substrate (fat or its decomposition products) and the products of the metabolism both form constituent elements of our food. The animal or vegetable fats that may be used in the invention include all those which can be emulsified at 30°–40°C in or with the culture medium, thus all the fats which are liquid at room temperature, and also pork fat, rancid fat, waste fat and suet. According to the invention the grown micro-organism is primarily a yeast. In this respect we favour the strains belonging to the Endomycetaceae family Saccharomycetoideae sub-family as well as the Cryptococcaceae family Cryptococcoideae sub-family, but of the members of the Fungi imperfecti group Deuteromycetes may also be employed.

Below we set out a few expediently usable micro-organisms. In the nomenclature of the yeasts we took as our base the work entitled "The Yeasts—a Taxonomic Study" (Looder and Kreger van Rij, 1967, publisher: North Holland Publishing Co. Amsterdam).

Yeasts: *Candida guilliermondii*
*Candida tropicalis*
*Candida lipolytica*
*Candida utilis* (also known as *Torula utilis, Torulopsis utilis*)
*Saccharomyces fragilis*
*Saccharomyces lactis*
Deuteromycetes
*Geotrichum candidum* (also known as *Oidium lactis*).

The cultivation of the yeasts is effected in a culture medium which, in addition to the fat serving as a source of carbon, contains also an ammonium salt or carbamide as a source of nitrogen, and other inorganic ions ($PO_4^{3-}$, $Cl^-$, $K^+$, $Na^+$, $Mg^{2+}$, $Ca^{2+}$, $Zn^{2+}$, $Mn^{2+}$, $Fe^{2+}$ and $Cu^{2+}$). From these the salts used as sources as nitrogen are employed in such concentrations that the nitrogen content of the culture medium is 0.1–0.2 %; the N:P ratio should be 4:1. The K- and Cl-ions are introduced into the culture solution in the form of KCl (0.1–0.2 %), the Mg and $SO_4$-ions as $MgSO_4$ (0.080–0.1 %). As trace elements Zn and Mn salts are added and the other ions are contained in sufficient quantities by the mains water used for the proliferation. If required for the proliferation of Saccharomyceses a material such as yeast extract containing growth factors may be expedient (10–25 mg/liter).

In order to avoid possible infections the proliferation is effected at a temperature of 30° to 40°C, at a pH of 4.5 to 5. To keep the pH at a constant value an alkaline pH aqueous medium (expediently dilute ammonium hydroxide) is introduced.

The supply of oxygen essential for proliferation is ensured by introducing air with the aid the usual Vegelbusch- or Lefrancois-type apparatuses or other apparatuses suitable for the manufacture of yeast. The intensity of the aeration is 150–300 $m^3$ per hour . $m^2$ fermenter base area.

At the end of the proliferation the fat is practically completely used up and in the usual way the yeast is separated from the aqueous medium with the aid of separators. The product obtained is suitable for further use in a pressed or dried form.

In this way, depending on the type of fat, 0.7 to 0.8 kg dry yeast is obtained per kg of fat with a protein content of at least 50 %, with an amino acid composition characteristic of yeast, and the fatty acid part of its lipids mirrors the type of the fat used. In addition to this the yeast also contains vitamins, among which the B-vitamin group is conspicuous but particularly the $B_2$, $B_6$ and $B_{12}$ vitamins and nicotinic acid and pantothenic acid.

As a consequence of the relatively neutral flavour of the obtained vitamin-protein concentrate it may be mixed in powder or tablet form in mass catering or in family food preparation into vegetables, pastries and cakes, and thus the daily protein and vitamin intake may be increased.

For dietetic preparations in the canning industry, vegetables and cakes it is possible to produce protein-rich products in an industrially usable and inexpensive manner which is a very important requirement for many illnesses, especially diabetes.

The amount of use depends on personal taste but is 200 g/kg preparation, at the most.

For the partial, from 25 to 50 %, or complete substitution of vegetable flours in meat products, sausages and pies (e.g. rice flour, potato flour etc.) serving primarily as a source of calories, because of their high starch content, a qualitatively superior product richer in protein may be produced.

The invention is illustrated but not limited by the following Examples.

EXAMPLE 1

The yeast fungus *Candida utilis* is proliferated in a culture medium containing 1 % pork fat. The yeast, maintained in a way usual in micro-biological practice, is cultivated in a vibrating retort culture and simultaneously it is adapted in a culture medium for the preparation of which the following were employed:

| | |
|---|---|
| pork fat | 1 % |
| ammonium sulphate | 0.5 % |
| superphosphate | 0.3 % |
| KCl | 0.1 % |
| $MgSO_4 \cdot 7 H_2O$ | 0.1 % |
| $ZnSO_4 \cdot 7 H_2O$ | 0.17 % |
| $MnSO_4 \cdot 7 H_2O$ | 0.005 %. |

After pre-proliferation for 24 to 48 hours at 30°C the yeast obtained serves as an inoculant. (Pre-treatment stage).

The culture medium containing inorganic salts is introduced into a proliferation vat and the aeration is started with an intensity of 150 to 300 m³ per hour per m² fermenter base area, and the fat is added which has been emulsified as follows: the fat is mixed with two to 10 times its quantity of culture solution containing inorganic salts and is heated to 50° to 70°C during mixing. After adding the fat emulsion to the proliferation vat the culture medium is inoculated with an inoculant-yeast in the amount of 10 to 20 % relative to the carbon source. (Growth stage)

The proliferation is carried out at 30° to 35°C and a pH of 4.5 to 5. To control the pH a 2 to 10 % aqueous ammonium hydroxide is used.

The proliferation terminates in 10 to 12 hours and the fat is completely consumed and transformed into yeast. The yield of dry yeast is 75 % relative to the added pork fat. The dry material composition of the product obtained is as follows:

| | |
|---|---|
| Protein | minimum 50 % |
| Lipids | 7 % |
| Ash | 6 % |
| Vitamins | |
| Thiamin ($B_1$) | minimum 3 mg/100 g |
| Riboflavin ($B_2$) | minimum 5 mg/100 g |
| Niacin | minimum 20 mg/100 g |
| Pyridoxin ($B_6$) | minimum 1.5 mg/100 g |
| Ergosterine ($D_2$ provitamin) | minimum 3 mg/100 g |

The yeast formed is separated from the aqueous medium in the usual manner by separators and is rendered storable by drying (drum or spray dryer).

EXAMPLE 2

*Candida guilliermodii* is proliferated and the fat is rancid pork fat in the amount of 3 %.

The culture medium is identical with the previous one but with a difference that the quality of the source of nitrogen and phosphorous is proportionally increased appropriately for the energy sources, in this case 0.+ % carbamide is used and 0.45 % superphosphate.

The proliferation is started as described in the first Example. Approximately 9 to 10 hours later, when the cell concentration reaches 1.2–1.5 %, continuous operation is commenced with an hourly recovery rate of 20 to 25 % and all the culture materials are replaced at a rate appropriate to that. The cell concentration during the further proliferation is 1.2 to 1.5 %.

The recovered yeast containing culture medium is treated as described in Example 1.

The characteristics of the proliferation and the quality of the yeast are as described in Example 1.

EXAMPLE 3

The yeast strain *Saccharomyces fragilis* is proliferated in a culture medium containing 2 % vegetable fat.

The culture medium contains 1 % ammonium sulphate and 0.6 % superphosphate, the quality and quantity of the other mineral salts are identical with those of Example 1. The proliferation is carried out in the manner described in Example 1 or 2 but with the difference that the proliferation temperature is 37°C.

The yeast containing culture medium is separated as described in Example 1 and dried.

The average composition of the product relative to the dry content is as follows:

| | |
|---|---|
| Protein | around 50 % |
| Lipids | 7 – 9 % |
| Ash | 4 – 6 % |
| Vitamins | |
| Thiamin ($B_1$) | 3 – 5 mg/100 g |
| Riboflavin ($B_2$) | 4 – 5 mg/100 g |
| Niacin (PP) | 25 – 30 mg/100 g |
| Pyridolin ($B_6$) | 2 – 3 mg/100 g |
| Ergosterin ($P_2$ provitamin) | 3 – 5 mg/100 g |

EXAMPLE 4

For the proliferation a mixed culture is used containing *Candida utilis* belonging to the sub-family Deuteromycetes and *Geotrichum candidum* belonging to Deuteromycetes.

The culture medium may contain any fat in the amount of 1 to 3 % and contains the salts described in Examples 1 to 3 in an amount corresponding to the concentration of fat (N and P sources, mineral salts).

The proliferation is started with *Candida utilis*. After the intensive acidification arising in the culture medium the latter is inoculated with *Geotrichum Candidum* and then the proliferation is carried out as already described in an intermittent or semi-continuous or continuous manner. The processing of the yeast containing culture medium is identical with that described in Example 1 to 4.

The composition of the obtained bio-mass is similar to that described in the preceding Examples with the difference that its protein content is somewhat lower (45 % approximately) while its lipid content is higher (10 to 15 %) than those of the preceding Examples.

EXAMPLE 5

10 to 20 g of dried yeast produced according to Examples 1 to 4 is uniformly mixed with 40 g grated potatoes, 2 g salt, 2.5 g milk powder, 100 to 120 ml water is added and the thus obtained mass is kneaded into a dough, from the dough rods are formed and the rods are baked and in this way a protein-enriched potato croquette is obtained.

EXAMPLE 6

To minced meat suitable for making meat loaf an equal amount of protein concentrate preparation according to Examples 1 to 4 is added and thus a preparation is obtained with a protein content 20 % greater than usual.

EXAMPLE 7

From the bio-mass produced according to Examples 1 to 4 20 g is mixed per portion into vegetables and thus a protein-enriched vegetable is obtained.

We claim:

1. A method for the production of a protein-vitamin concentrate suitable for human consumption or animal feeding and having a protein content of at least 50% by weight, comprising culturing a member selected from the group consisting of *Candida guilliermondic, Candida tropicalis, Candida lipolytica, Candida utilis, Saccharomyces fragilis, Saccharomyces lactis*, Deuteromycetes and *Geotrichum candidum* in a culture medium containing animal or vegetable fat as a carbon and energy source, ammonium salt or carbamide as a source of nitrogen, the nitrogen content of the medium being 0.1 to 0.2%, mineral material providing the ions $PO_4^{3-}$, $Cl^-$, $K^+$, $Na^+$, $Mg^{2+}$, $Ca^{2+}$, $Mn^{2+}$, $Fe^{2+}$ and $Cu^{2+}$, the N:P ratio being about 4:1, the pH being about 4.5 to 5 and the temperature being about 30° to 40°C., aerating the culture medium at an aeration intensity of about 150 to 300 cubic meters of air per square meter of fermenter base area per hour, and separating the resulting biomass from the culture medium.

2. A method as claimed in claim 1, in which said fat is directly emulsified with the culture medium.

3. A method as claimed in claim 1, said fat being selected from the group consisting of pork fat, rancid fat, waste fat and suet.

4. A method as claimed in claim 1, in which the culture medium contains about 0.1–0.2% KCl and about 0.080–0.1% $MgSO_4$.

* * * * *